US009926339B2

(12) United States Patent
Fujita et al.

(10) Patent No.: US 9,926,339 B2
(45) Date of Patent: Mar. 27, 2018

(54) FLUORINE-CONTAINING SILANE COMPOUND

(71) Applicants: MITSUBISHI MATERIALS CORPORATION, Tokyo (JP); Mitsubishi Materials Electronic Chemicals Co., Ltd., Akita-shi (JP)

(72) Inventors: Masato Fujita, Akita (JP); Daisuke Takano, Saitama (JP); Masakazu Uotani, Akita (JP); Takeshi Kamiya, Akita (JP); Tsunetoshi Honda, Akita (JP)

(73) Assignees: MITSUBISHI MATERIALS CORPORATION, Tokyo (JP); MITSUBISHI MATERIALS ELECTRONIC CHEMICALS CO., LTD, Akita-shi (JP)

( * ) Notice: Subject to any disclaimer, the term of this patent is extended or adjusted under 35 U.S.C. 154(b) by 0 days.

(21) Appl. No.: 15/129,556

(22) PCT Filed: Mar. 31, 2015

(86) PCT No.: PCT/JP2015/060192
§ 371 (c)(1),
(2) Date: Jan. 31, 2017

(87) PCT Pub. No.: WO2015/152265
PCT Pub. Date: Oct. 8, 2015

(65) Prior Publication Data
US 2017/0145039 A1    May 25, 2017

(30) Foreign Application Priority Data

Mar. 31, 2014 (JP) ................................. 2014-073517
Mar. 31, 2014 (JP) ................................. 2014-073518

(51) Int. Cl.
*C03C 17/30* (2006.01)
*C07F 7/18* (2006.01)
*C09D 5/00* (2006.01)

(52) U.S. Cl.
CPC ............ *C07F 7/1836* (2013.01); *C03C 17/30* (2013.01); *C09D 5/00* (2013.01); *C03C 2217/76* (2013.01)

(58) Field of Classification Search
CPC combination set(s) only.
See application file for complete search history.

(56) References Cited

U.S. PATENT DOCUMENTS

| | | | |
|---|---|---|---|
| 3,646,085 A | 2/1972 | Bartlett | |
| 3,944,587 A | 3/1976 | Katsushima et al. | |
| 2014/0234543 A1* | 8/2014 | Ito ........................ | B05D 3/107 427/341 |

FOREIGN PATENT DOCUMENTS

| | | |
|---|---|---|
| CN | 1315483 A | 10/2001 |
| JP | 49-126625 A | 12/1974 |
| JP | 08-319115 A | 12/1996 |
| JP | 11-029585 A | 2/1999 |
| JP | 11-217561 A | 8/1999 |
| JP | 2000-169483 A | 6/2000 |
| JP | 2000-248114 A | 9/2000 |
| JP | 3342170 B2 | 11/2002 |
| JP | 2004-300047 A | 10/2004 |
| JP | 2005-002000 A | 1/2005 |
| JP | 3619724 B2 | 2/2005 |
| JP | 2008-297275 A | 12/2008 |
| JP | 2009-143881 A | 7/2009 |
| JP | 2010-540644 A | 12/2010 |
| JP | 2011-505422 A | 2/2011 |
| JP | 2011-074080 A | 4/2011 |
| JP | 2012-017291 A | 1/2012 |
| WO | 2009/045771 A2 | 4/2009 |
| WO | 2009/073595 A1 | 6/2009 |
| WO | 2009/101986 A1 | 8/2009 |

OTHER PUBLICATIONS

"Effect of use of silane coupling agent," S&T Publishing, 2012, pp. 290-304 and partial English translation thereof.
Norio Yoshino et al., "Syntheses and Reactions of Metal Organics. XVIII. Syntheses of (1H,1H,2H,2H-Polyfluoroalkyl)trimethoxysilanes and Surface Modification of Glass Plate," Bull. Chem. Soc. Jpn., 1993, 66, pp. 1754-1758.
International Search Report dated Jun. 23, 2015, issued for PCT/JP2015/060192 and English translation thereof.
Office Action dated Dec. 9, 2014, issued for the Japanese patent application No. 2014-073517 and English translation thereof.
Office Action dated Dec. 9, 2014, issued for the Japanese patent application No. 2014-073518 and English translation thereof.
Supplementary European Search Report dated Jul. 27, 2017, issued for the European patent application No. 15773555.6.

* cited by examiner

*Primary Examiner* — Amanda L Aguirre
(74) *Attorney, Agent, or Firm* — Locke Lord LLP

(57) ABSTRACT

A novel fluorine-containing silane compound is provided. The fluorine-containing silane compound is capable of providing excellent water repellency and oil repellency, and is useful as a fluorine-containing silane coupling agent with applicability to a wide variety of applications, even if it has a chemical structure, which is free of a perfluoroalkyl group of 8 or more of carbon atoms; and has no risk of formation of PFOS or PFOA causing bioaccumulation potential and environment adaptability problems. A fluorine-containing silane compound containing at least one of each of a nitrogen-containing perfluoroalkyl group and an alkoxysilyl group in the molecule is selected.

2 Claims, No Drawings

FLUORINE-CONTAINING SILANE COMPOUND

TECHNICAL FIELD

The present invention relates to a novel fluorine-containing silane compound.

Priority is claimed on Japanese Patent Application No. 2014-073517 and Japanese Patent Application No. 2014-073518, filed Mar. 31, 2014, the contents of which are incorporated herein by reference.

BACKGROUND ART

Conventionally, various silane compounds have been used as the silane coupling agent in order to improve adhesiveness on the interface between organic and inorganic materials. In addition, the silane coupling agent is utilized as a surface preparation agent of organic and inorganic materials; and it is known that the silane coupling agent can provide various functions on the surface of the material.

Among them, the fluorine-containing silane coupling agent is used in various fields as agents providing slipperiness, detachability, water repellency, and oil repellency; and particularly the fluorine-containing silane coupling agents containing a perfluoroalkyl group of 8 or more carbon atoms have been utilized (refer Patent Literature 1 (PTL 1) and Patent Literature 2 (PTL 2), for example).

However, in recent years, it has shown that the perfluorooctane sulfonic acid (PFOS) or the perfluorooctanoic acid (PFOA), which has toxicity and high environment-bio accumulation potentials, can be formed by decomposing the compound containing the perfluoroalkyl group of 8 or more carbon atoms. Thus, there is a problem that restriction has been imposed on the usage of these compounds. Therefore, there is a demand for a material, which will not structurally form PFOS or PFOA with high environment-bio accumulation potentials; has the shortest possible perfluoroalkyl group structure of 6 or less carbon atoms, in the market.

Under the above-described circumstance, a silane compound with a short chain length structure, in which the number of carbon atoms of the perfluoroalkyl group is reduced simply, is proposed (refer PTLs 1 and 2, for example). According to this silane compound with the short chain length structure, there is no risk on the environment since PFOS or PFOA is not formed if it is decomposed.

However, in the fluorine-containing silane coupling agent using this silane compound with the simple short chain length structure, there is a problem that one comparable to the above-described conventional fluorine-containing silane coupling agent containing the perfluoroalkyl group of 8 or more carbon atoms cannot be obtained in terms of the properties of slipperiness, detachability, water repellency, and the like.

CITATION LIST

Patent Literature

PTL 1: Japanese Patent (Granted) Publication No. 3342170 (B)
PTL 2: Japanese Patent (Granted) Publication No. 3619724 (B)

Non Patent Literature

NPL 1: "Effect of use of silane coupling agent" S&T Publishing, pages 290-304 (Published in year 2012)
NPL 2: Bull. Chem. Soc. Jpn. 1993, 66, 1754-1758

SUMMARY OF INVENTION

Technical Problem

The present invention is made under the circumstances described above. The purpose of the present invention is to provide a novel fluorine-containing silane compound, which is capable of providing excellent water repellency and oil repellency can be obtained; is useful as a fluorine-containing silane coupling agent with applicability to a wide variety of applications, even if it has a chemical structure, which is free of a perfluoroalkyl group of 8 or more of carbon atoms; and has no risk of formation of PFOS or PFOA causing bioaccumulation potential and environment adaptability problems.

Solution to Problem

In order to solve the above-mentioned problems, the present invention has the aspects described below.

(1) A fluorine-containing silane compound comprising a perfluoroamine structure represented by a general formula (1) or a general formula (A1) below.

[Chemical formula 1]

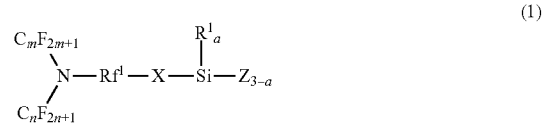

(1)

[Chemical formula 2]

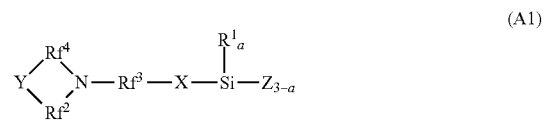

(A1)

In the general formula (1), m and n are integers from 1 to 6, which are identical or different; $Rf^1$ is a straight-chain or a branched-chain perfluoroalkylene group of 1 to 6 carbon atoms.

In the general formula (A1), $Rf^2$, $Rf^3$, and $Rf^4$ are straight-chain or branched-chain perfluoroalkylene groups of 1 to 6 carbon atoms.

In the general formula (1) and the general formula (A1), X is a hydrocarbon group of 2 to 10 carbon atoms and includes one or more selected from an ether bond, a CO—NH bond, and an O—CO—NH bond.

In the general formula (1) and the general formula (A1), $R^1$ and Z are an alkoxy group or a halogen group, a being an integer from 0 to 3.

(2) The fluorine-containing silane compound according to the above-described (1), wherein the Z is the alkoxy group.

Advantageous Effects of Invention

The fluorine-containing silane compound of the present invention is capable of providing excellent water repellency and oil repellency, and is useful as a fluorine-containing silane coupling agent with applicability to a wide variety of applications, even if it has a chemical structure, which is free of a perfluoroalkyl group of 8 or more of carbon atoms; and has no risk of formation of PFOS or PFOA causing bioaccumulation potential and environment adaptability problems.

DESCRIPTION OF EMBODIMENTS

The fluorine-containing silane compound, which is an embodiment of the present invention, is explained below with a producing method thereof and a utilization method as a fluorine-containing silane coupling agent in details.

[First Embodiment]
[Fluorine-Containing Silane Compound]

First, the configurations of the fluorine-containing silane compound, which is the first embodiment of the present invention, are explained.

In terms of the fluorine-containing silane compound of the present embodiment, it is not particularly limited as long as the fluorine-containing silane compound has the structure containing one of each of a nitrogen-containing perfluoroalkyl group and an alkoxysilyl group in the molecule.

In terms of the configuration of the fluorine-containing silane compound of the present embodiment, specifically, it can be represented by the general formula (1) shown below.

[Chemical formula 3]

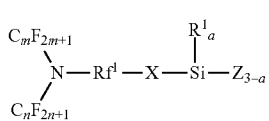

(1)

In the general formula (1), m and n are integers from 1 to 6, which are identical or different. $Rf^1$ may be a perfluoroalkylene group of 1 to 6 carbon atoms; and a straight-chain or a branched-chain.

In the general formula (1), X may be a di-valent organic group and a hydrocarbon group of 2 to 10 carbon atoms; and may include one or more selected from an ether bond, an ester bond, an amide bond, and a urethane bond.

In addition, in the general formula (1), $R^1$ is a lower alkyl group or a phenyl group; and Z is a hydrolyzable group, the subfix "a" being an integer from 0 to 3.

As specific examples of the nitrogen-containing perfluoroalkyl group in the above-indicated general formula (1), perfluoroamine structures shown by formulae (2) to (13) are presented.

[Chemical formula 4]

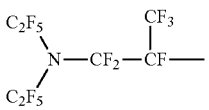

(2)

[Chemical formula 5]

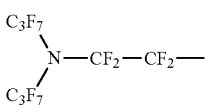

(3)

[Chemical formula 6]

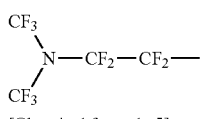

(4)

[Chemical formula 7]

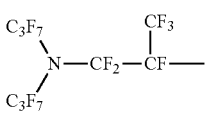

(5)

[Chemical formula 8]

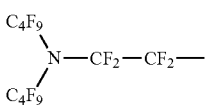

(6)

[Chemical formula 9]

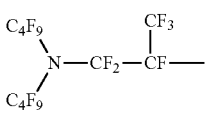

(7)

[Chemical formula 10]

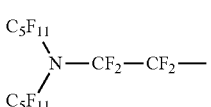

(8)

[Chemical formula 11]

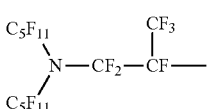

(9)

[Chemical formula 12]

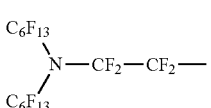

(10)

[Chemical formula 13]

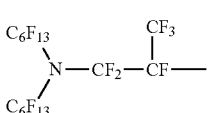

(11)

[Chemical formula 14]

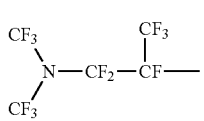

(12)

[Chemical formula 15]

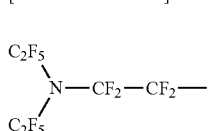

(13)

In addition, as examples of X in the above-indicated general formula (1), structures shown by formulae (14) to (17) are presented. The formulae (14), (15), (16), and (17) show examples of an ether bond, an ester bond, an amide bond, and a urethane bond, respectively.

[Chemical formula 16]

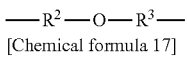  (14)

[Chemical formula 17]

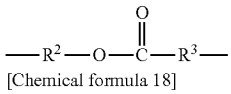  (15)

[Chemical formula 18]

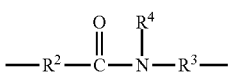  (16)

[Chemical formula 19]

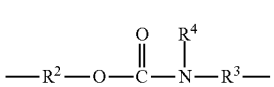  (17)

In the above-indicated formulae (14) to (17), $R^2$ and $R^3$ are hydrocarbon groups of 0 to 10 carbon atoms; and $R^4$ is a hydrogen atom or a hydrocarbon group of 1 to 6 carbon atoms.

In the general formula (1), $R^1$ is a lower alkyl group such as a methyl group, an ethyl group, a propyl group, a butyl group, and the like; or a phenyl group. Among them, choosing the methyl group is more preferable.

In the general formula (1), Z is not particularly limited as long as it is a hydrolyzable group that is capable of forming Si—O—Si bond after hydrolysis. As specific examples of the hydrolyzable group, the alkoxy group such as a methoxy group, an ethoxy group, a propoxy group, a butoxy group, and the like; the halogen group such as a chlorine group, bromo group, an iodine group, and the like; the aryloxy group such as phenoxy group, a naphthoxy group, and the like; the aralkyloxy group such as a benzyloxy group, a phenethyloxy group, and the like; the acyloxy group such as an acetoxy group, a propionyloxy group, a butyryloxy group, a valeryloxy group, a pivaloyloxy group, benzoyloxy group, and the like; or the like are named, for example. Among them, choosing the methoxy group, the ethoxy group, or the chloro group is preferable.

As specific examples of the fluorine-containing silane compound having the perfluoroamine structure represented by the general formula (1), the structures shown by formulae (18) to (65) are presented below.

R is a methyl group or an ethyl group in the formulae (18) to (65) below.

[Chemical formula 20]

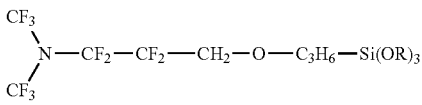  (18)

[Chemical formula 21]

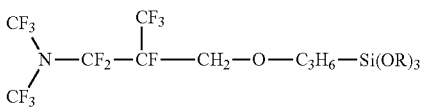  (19)

[Chemical formula 22]

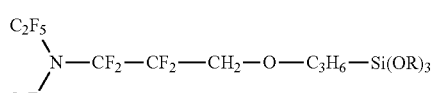  (20)

[Chemical formula 23]

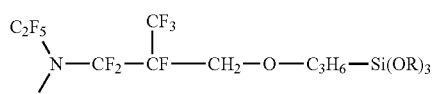  (21)

[Chemical formula 24]

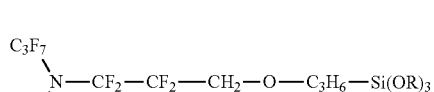  (22)

[Chemical formula 25]

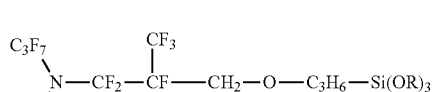  (23)

[Chemical formula 26]

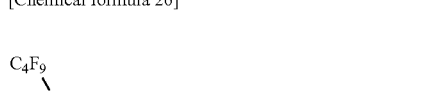  (24)

[Chemical formula 27]

  (25)

[Chemical formula 28]

  (26)

[Chemical formula 29]

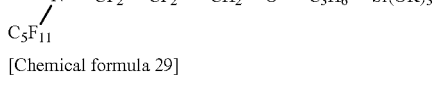  (27)

[Chemical formula 30]

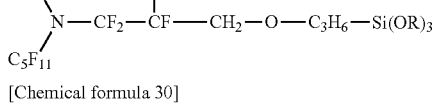  (28)

[Chemical formula 31]

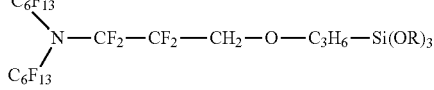  (29)

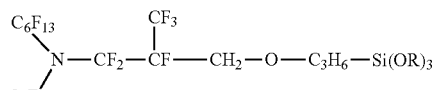

[Chemical formula 32]
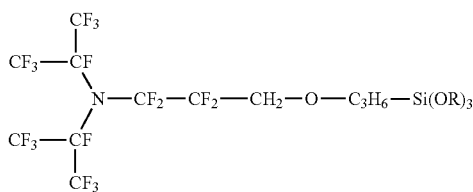
(30)
[Chemical formula 33]
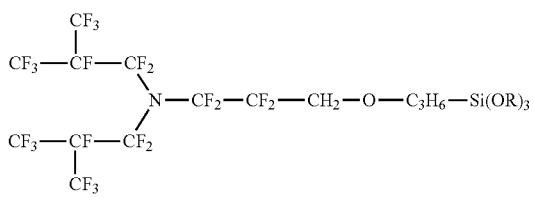
(31)
[Chemical formula 34]
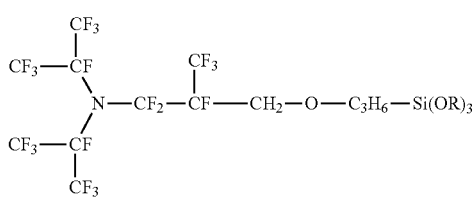
(32)
[Chemical formula 35]
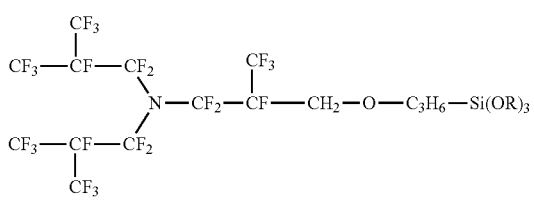
(33)
[Chemical formula 36]
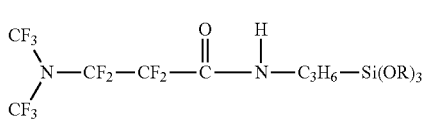
(34)
[Chemical formula 37]
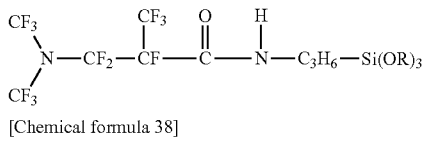
(35)
[Chemical formula 38]
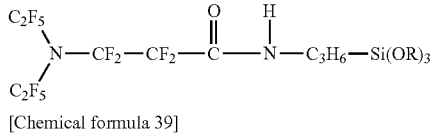
(36)
[Chemical formula 39]
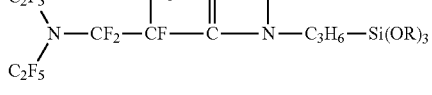
(37)
[Chemical formula 40]
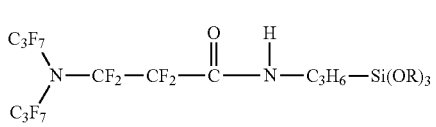
(38)
[Chemical formula 41]
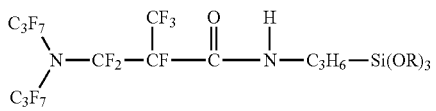
(39)
[Chemical formula 42]
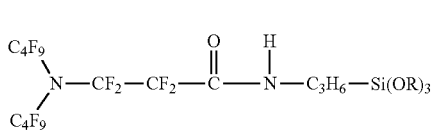
(40)
[Chemical formula 43]
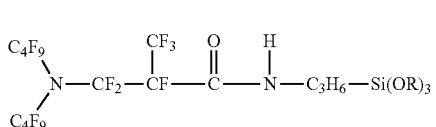
(41)
[Chemical formula 44]
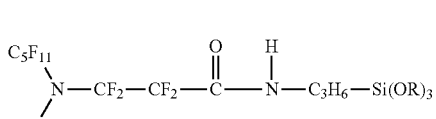
(42)
[Chemical formula 45]
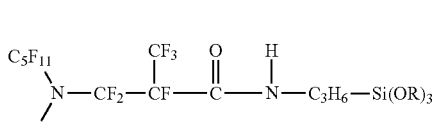
(43)
[Chemical formula 46]
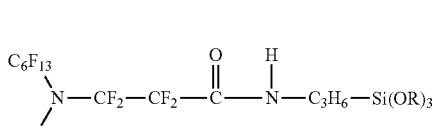
(44)
[Chemical formula 47]
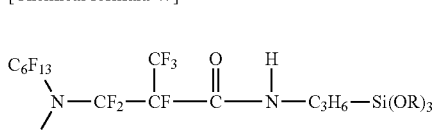
(45)
[Chemical formula 48]
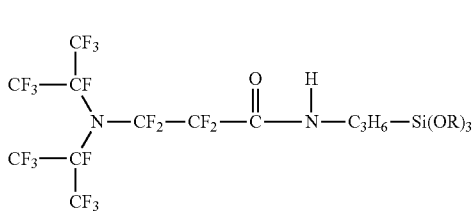
(46)

-continued
[Chemical formula 49]
(47)
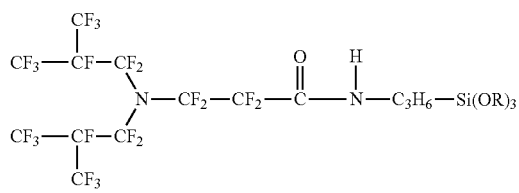
[Chemical formula 50]
(48)
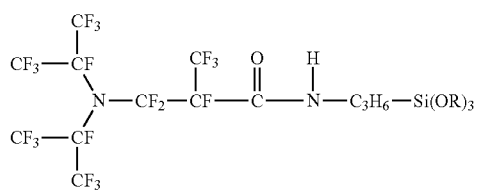
[Chemical formula 51]
(49)
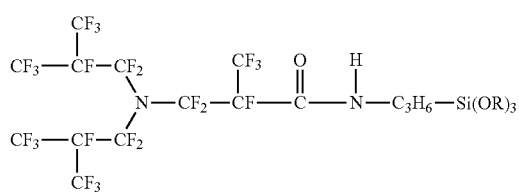
[Chemical formula 52]
(50)
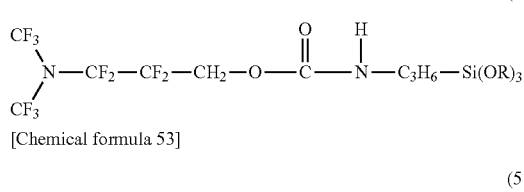
[Chemical formula 53]
(51)
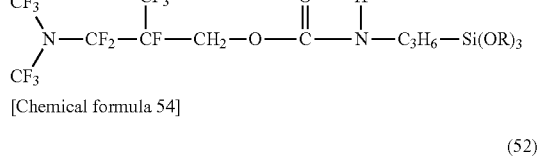
[Chemical formula 54]
(52)
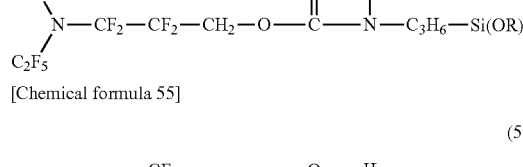
[Chemical formula 55]
(53)
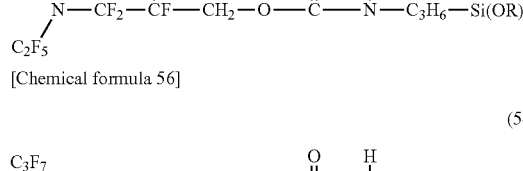
[Chemical formula 56]
(54)
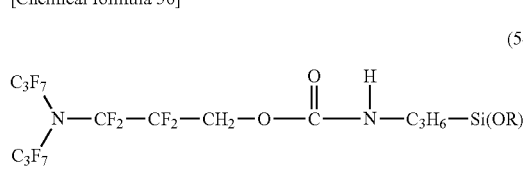
-continued
[Chemical formula 57]
(55)
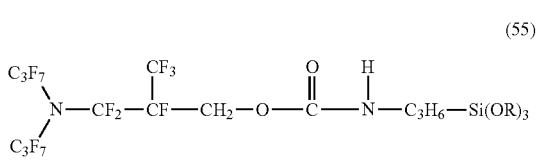
[Chemical formula 58]
(56)
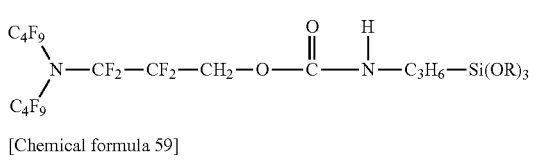
[Chemical formula 59]
(57)
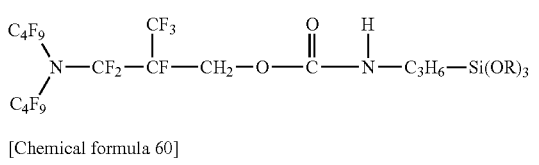
[Chemical formula 60]
(58)
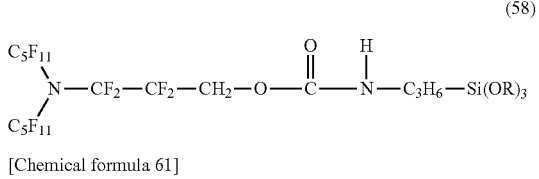
[Chemical formula 61]
(59)
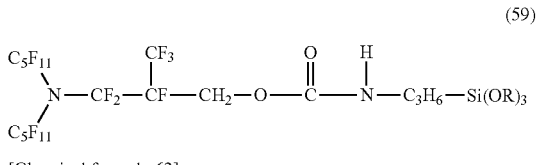
[Chemical formula 62]
(60)
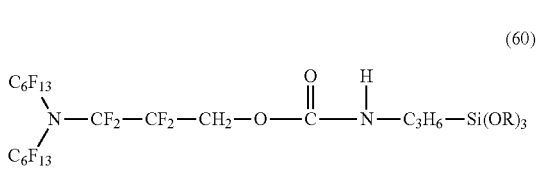
[Chemical formula 63]
(61)
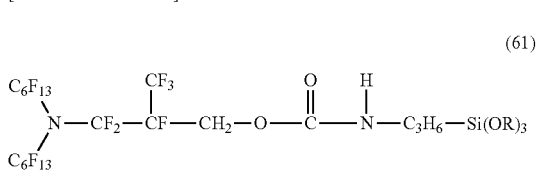
[Chemical formula 64]
(62)
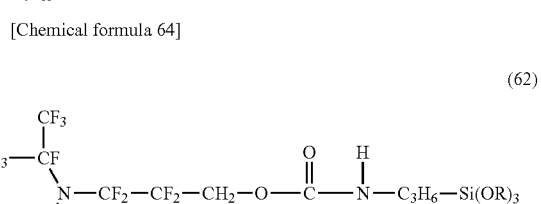
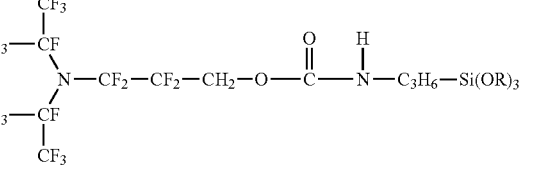

-continued

[Chemical formula 65]

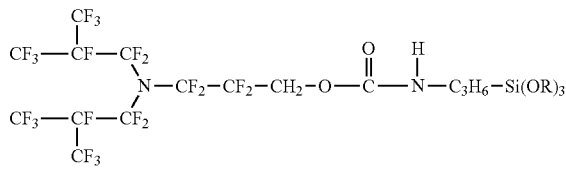
(63)

[Chemical formula 66]

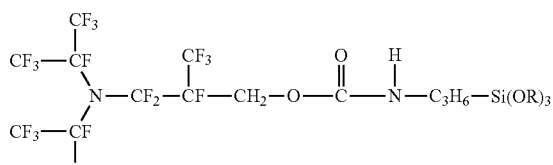
(64)

[Chemical formula 67]

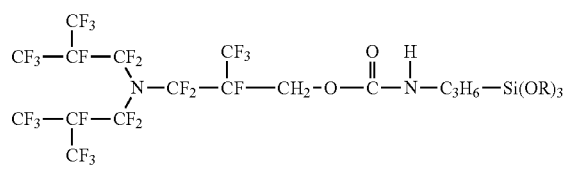
(65)

As described above, according to the fluorine-containing silane compound of the present embodiment, the fluorine-containing silane compound has the structure containing one or more of each of the nitrogen-containing perfluoroalkyl group and the alkoxysilyl group in the molecule. More specifically, the structure of the fluorine-containing silane compound contains the nitrogen-containing perfluoroalkyl group in which multiple short-chain length perfluoroalkyl groups of 6 or less carbon atoms are bonded to a nitrogen atom. Since the fluorine content in the molecule is high in the structure, it can provide excellent water repellency and oil repellency. On the other hand, it has the chemical structure with no risk of formation of PFOS or PFOA, which could possibly be a problem in terms of the bioaccumulation potential and the environment adaptability, even in the case where it is degraded, since the structure is free of the perfluoroalkyl group of 8 or more carbon atoms in the molecule.

As explained above, the fluorine-containing silane compound of the present embodiment is a novel compound having excellent properties, and useful as a fluorine-containing silane coupling agent. In other words, the fluorine-containing silane compound of the present embodiment is designed to satisfy both of the excellent water/oil repellency and the environment adaptability; and it cannot be conceived easily from the compound constituting the conventional fluorine-containing silane coupling agent.

In addition, the fluorine-containing silane compound of the present embodiment contains the perfluoroamine structure, in which multiple short-chain length structures are branched out from a nitrogen atom, as the nitrogen-containing perfluoroalkyl group. Since this perfluoroamine structure is sterically bulky, the fluorine-containing silane compound can provide the excellent properties such as: high water/oil repellency; high antifouling property; high fingerprint resistance; high releasing property; high moisture resistance; high water resistance; high heat resistance; and the like, due to the fluorine group, compared to the fluorine-containing silane compound having a straight-chain perfluoroalkyl structure of less carbon atoms, although it only contains the perfluoroalkyl group of the short-chain length structure.

[Method of Producing the Fluorine-Containing Silane Compound]

Next, an example of the method of producing the fluorine-containing silane compound of the present embodiment is explained.

In the method of producing the fluorine-containing silane compound of the present embodiment, the fluorine-containing silane compound is obtained: by reducing the carboxylic acid halide containing the nitrogen-containing perfluoroalkyl group represented by the formula (66) shown below to alcohol; and by allowing the alcohol to react with isocyanate in the presence of a metallic catalyst after the reduction.

[Chemical formula 68]

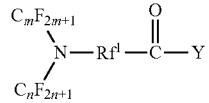
(66)

In the formula (66), m and n are integers from 1 to 6, which are identical or different. $Rf^1$ may be a perfluoroalkylene group of 1 to 6 carbon atoms, and a straight-chain or a branched-chain. In addition, Y is a halogen atom selected from the group consisting of fluorine, chlorine, bromine, and iodine.

The carboxylic acid halide containing the nitrogen-containing perfluoroalkyl group represented by the formula (66) shown above can be obtained by electrolytically fluorinating corresponding carboxylic acid ester or halide in hydrogen fluoride, for example. In the case where a halogen atom other than fluorine atom is used as the Y, it can be obtained: by performing hydrolysis treatment on the carboxylic acid fluoride containing the perfluoroalkyl group obtained by the above-described electrolytic fluorination to form the corresponding carboxylic acid; and then by allowing the formed carboxylic acid to react with a suitable halogenating agent (for example, thionyl chloride, oxalyl chloride, phosphoryl chloride, sulfuryl chloride, phosphorus trichloride, phosphorus pentachloride, phosphorus tribromide, phosphorus pentabromide, hydrogen bromide, hydrogen iodide, and the like) to derive the corresponding carboxylic acid halide, for example.

Cases, in which Xs are compounds having the ether bond, the amide bond, and the urethane bond in the general formula (1), are explained below.

[Case, in which X is a Compound Having the Urethane Bond]

In this case, X can be synthesized by the two-step reaction below, for example.

[Reduction Reaction of the Carboxylic Halide]

The carboxylic acid halide represented by the formula (66) is subjected to a reduction reaction by dropping a reducing agent, which is typified by lithium aluminum hydride ($LiAlH_4$), sodium borohydride ($NaBH_4$), and the like, to a solvent or a dispersed organic solvent, for example. By this reduction reaction, the alcohol represented by the formula (67) below is obtained.

[Chemical formula 69]

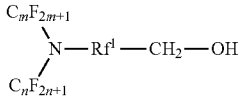
(67)

In the formula (67), m and n are integers from 1 to 6, which are identical or different. $Rf^1$ may be a perfluoroalkylene group of 1 to 6 carbon atoms, and a straight-chain or a branched-chain.

[Reaction with Isocyanate]

The fluorine-containing silane compound represented by the general formula (1) above is obtained by allowing the alcohol represented by the formula (67) obtained by the above-described reduction reaction to react to trialkoxysilane, which is a silane coupling agent containing an isocyanate group in an organic solvent.

As examples of the silane coupling agent containing the isocyanate group, triethoxysilylpropyl isocyanate, trimethoxysilylpropyl isocyanate, and the like can be presented.

In the reaction, a catalyst may be added in order to accelerate the reaction. As specific examples, the metal catalyst such as dibutyltin dilaurate, dibutyltin diacetate, tin octylate, bismuth octylate, decanoic acid bismuth, lead naphthenate, potassium acetate, and the like; the amine-based catalyst such as triethylamine, tripropylamine, triethylenediamine, diazabicycloundecene, and the like; the trialkyl phosphine catalyst; and the like can be presented.

[Case, in which X is a Compound Having the Ether Bond]
[Formation of Allyl Ether Body]

In this case, first, the allyl ether body represented by the formula (68) is obtained by allowing the alcohol represented by the formula (67) obtained by reducing the carboxylic acid halide containing the fluoroalkyl group as in the case of the compound having the urethane bond, to react to allyl halide (for example, allyl bromide, allyl chloride, and the like).

[Chemical formula 70]

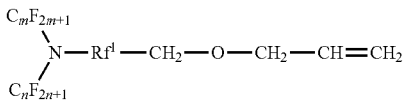
(68)

[Hydrosilylation Reaction]

Next, the fluorine-containing silane compound represented by the general formula (1) is obtained by allowing the obtained allyl ether body to react (hydrosilylation reaction using a platinum catalyst) to a silane compound (for example, trimethoxysilane, triethoxysilane, trichlorosilane, and the like).

[Case, in which X is a Compound Having the Amide Bond]
[Formation of Allyl Amide Body]

In this case, first, the allyl amide body represented by the formula (69) below is obtained by allowing the carboxylic acid halide containing the nitrogen-containing perfluoroalkyl group represented by the formula (66) above to react to allyl amine (for example, allyl amine, N-methyl allyl amine, and the like).

In the formula (69) below, R is a hydrogen atom, a hydrocarbon group of 1 to 6 carbon atoms, or the like.

[Chemical formula 71]

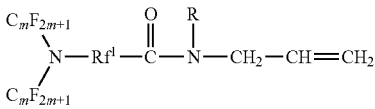
(69)

[Hydrosilylation Reaction]

Next, the fluorine-containing silane compound represented by the general formula (1) is obtained by allowing the obtained allyl amide body to react (hydrosilylation reaction using a platinum catalyst) to a silane compound (for example, trimethoxysilane, triethoxysilane, trichlorosilane, and the like).

[Utilization Method as a Fluorine-Containing Silane Coupling Agent]

Next, utilization method of the fluorine-containing silane compound as a fluorine-containing silane coupling agent is explained.

The fluorine-containing silane compound of the present embodiment can be used as a fluorine-containing silane coupling agent directly or after diluting by a medium as other component.

As the dilution medium used as the other component, liquid media such as organic solvents and water can be named. Specifically, as the concentration of the fluorine-containing silane compound in the dilution medium, it may be 0.01 to 100 mass %, for example. Preferably, the concentration is in the range of 0.01 to 50 mass %.

The organic solvent applicable to the fluorine-containing silane coupling agent of the present embodiment is not particularly limited. Specifically, the alcohol solvent such as methanol, ethanol, isopropyl alcohol, and the like; the ketone solvent such as acetone, methyl ethyl ketone; the ester solvent such as ethyl acetate, butyl acetate, and the like; the fluorine-based solvent such as α, α, α-trifluoro toluene, 1,3-bis trifluoromethyl benzene, 1,4-bis trifluoromethyl benzene, perfluorooctane, perfluorohexane, HCFC-225, HFC-365, methyl perfluoropropyl ether, methyl perfluoroalkyl ether, ethyl perfluorobutyl ether, hexafluoroisopropanol, and the like; and the like can used.

In addition, acid or alkaline (for example, hydrochloric acid, sulfuric acid, and nitric acid as the acid, and ammonia and the like as the alkaline) may be included in the fluorine-containing silane coupling agent other than the above-described fluorine-containing silane compound as the other component.

The fluorine-containing silane coupling agent of the present embodiment can be suitably used: as the coating agent providing properties such as effervescent, antifouling property, wiring resistance, water/oil repellency, releasing property, moisture resistance, water resistance, lubricity, heat resistance, and the like; as the surface preparation agent of the additives of the paint providing heat resistance; the migration inhibitor of the electronic components or circuits such as the silver paste, metal nano wiring, and the like; as the synthetic raw material of plastics; and the like.

Particularly, in the fluorine-containing silane coupling agent of the present embodiment, the fluorine-containing silane compound contains the perfluoroamine structure, in which multiple short-chain length structures are branched out from a nitrogen atom, as the nitrogen-containing perfluoroalkyl group. Since this perfluoroamine structure is sterically bulky, when it is used as a silane coupling agent, the fluorine-containing silane compound can provide the above-described excellent properties such as high water/oil repellency due to the fluorine group, compared to the fluorine-containing silane compound having a straight-chain perfluoroalkyl structure of less carbon atoms, although it only contains the perfluoroalkyl group of the short-chain length structure.

When it is used in applications, one kind of the fluorine-containing silane coupling agent of the present embodiment may be used. Alternatively, two different kinds of the fluorine-containing silane coupling agents may be used at the same time. Moreover, it may be used as a mixture with a component other than the fluorine-containing silane coupling agent.

As explained above, the fluorine-containing silane compound of the present embodiment is capable of providing excellent water repellency and oil repellency, and is useful as a fluorine-containing silane coupling agent with applicability to a wide variety of applications, even if it has a chemical structure, which is free of a perfluoroalkyl group of 8 or more of carbon atoms; and has no risk of formation of PFOS or PFOA causing bioaccumulation potential and environment adaptability problems.

[Second Embodiment]
[Fluorine-Containing Silane Compound]

Next, the configurations of the fluorine-containing silane compound, which is the second embodiment of the present invention, are explained.

In terms of the fluorine-containing silane compound of the present embodiment, it is not particularly limited as long as the fluorine-containing silane compound has the structure containing one of each of a nitrogen-containing perfluoroalkyl group and an alkoxysilyl group in the molecule.

In terms of the configuration of the fluorine-containing silane compound of the present embodiment, specifically, it can be represented by the general formula (A1) shown below.

[Chemical formula 72]

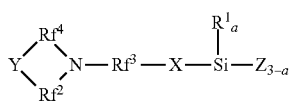

(A1)

In the general formula (A1), $Rf^4$, $Rf^2$, and $Rf^3$ are identical or different perfluoroalkylene groups of 1 to 6 carbon atoms. Each of them may be a straight-chain or a branched-chain. In addition, Y is an oxygen atom, a nitrogen atom, or a $CF_2$ group.

In the general formula (A1), X may be a di-valent organic group and a hydrocarbon group of 2 to 10 carbon atoms; and may include one or more selected from an ether bond, an ester bond, an amide bond, and a urethane bond.

In addition, in the general formula (A1), $R^1$ is a lower alkyl group or a phenyl group; and Z is a hydrolyzable group, the suffix "a" being an integer from 0 to 3.

As specific examples of the nitrogen-containing perfluoroalkyl group in the above-indicated general formula (A1), structures containing: perfluoroalkyl piperidine; perfluoroalkyl pyrrolidine; perfluoroalkyl piperazine; perfluoroalkyl morpholine; and perfluoroalkyl hexamethyleneimine, as a perfluorinated heterocyclic ring, shown by formulae (A2) to (A13) are presented.

[Chemical formula 73]

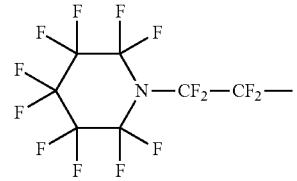

(A2)

[Chemical formula 74]

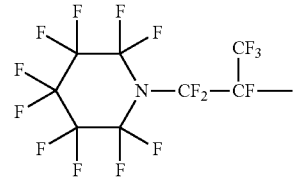

(A3)

[Chemical formula 75]

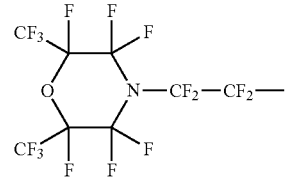

(A4)

[Chemical formula 76]

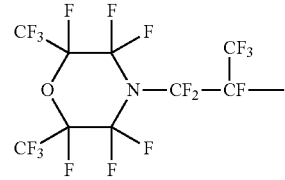

(A5)

[Chemical formula 77]

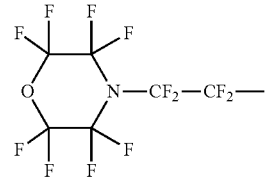

(A6)

[Chemical formula 78]

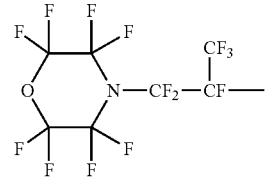

(A7)

[Chemical formula 79]

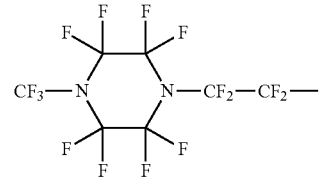

(A8)

[Chemical formula 80]

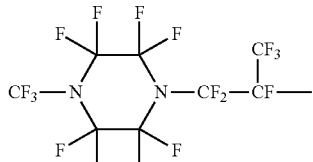
(A9)

[Chemical formula 81]

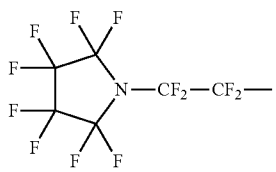
(A10)

[Chemical formula 82]

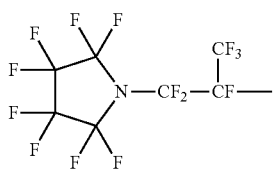
(A11)

[Chemical formula 83]

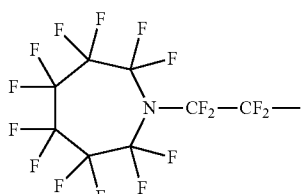
(A12)

[Chemical formula 84]

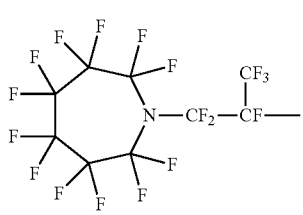
(A13)

In addition, as examples of X in the above-indicated general formula (A1), structures shown by formulae (A14) to (A17) are presented. The formulae (A14), (A15), (A16), and (A17) show examples of an ether bond, an ester bond, an amide bond, and a urethane bond, respectively.

[Chemical formula 85]

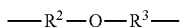
(A14)

[Chemical formula 86]

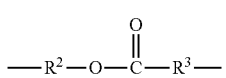
(A15)

[Chemical formula 87]

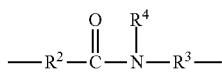
(A16)

[Chemical formula 88]

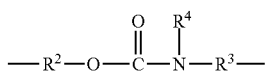
(A17)

In the above-indicated formulae (A14) to (A17), $R^2$ and $R^3$ are hydrocarbon groups of 0 to 10 carbon atoms; and $R^4$ is a hydrogen atom or a hydrocarbon group of 1 to 6 carbon atoms.

In the general formula (A1), $R^1$ is a lower alkyl group such as a methyl group, an ethyl group, a propyl group, a butyl group, and the like; or a phenyl group. Among them, choosing the methyl group is more preferable.

In the general formula (A1), Z is not particularly limited as long as it is a hydrolyzable group that is capable of forming Si—O—Si bond after hydrolysis. As specific examples of the hydrolyzable group, the alkoxy group such as a methoxy group, an ethoxy group, a propoxy group, a butoxy group, and the like; the halogen group such as a chlorine group, bromo group, an iodine group, and the like; the aryloxy group such as phenoxy group, a naphthoxy group, and the like; the aralkyloxy group such as a benzyloxy group, a phenethyloxy group, and the like; the acyloxy group such as an acetoxy group, a propionyloxy group, a butyryloxy group, a valeryloxy group, a pivaloyloxy group, benzoyloxy group, and the like; or the like are named, for example. Among them, choosing the methoxy group, the ethoxy group, or the chloro group is preferable.

As specific examples of the fluorine-containing silane compound having the perfluorinated heterocyclic ring represented by the general formula (A1), the structures shown by formulae (A18) to (A80) are presented below.

R is a methyl group or an ethyl group in the formulae (A18) to (A80) below.

[Chemical formula 89]

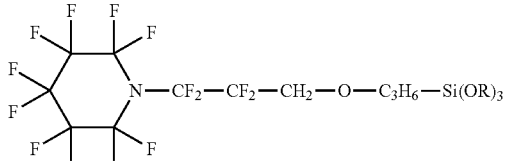
(A18)

[Chemical formula 90]

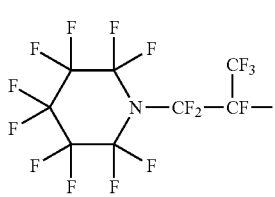
(A19)

[Chemical formula 91]
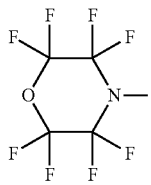  —CF$_2$—CF$_2$—CH$_2$—O—C$_3$H$_6$—Si(OR)$_3$ (A20)
[Chemical formula 92]
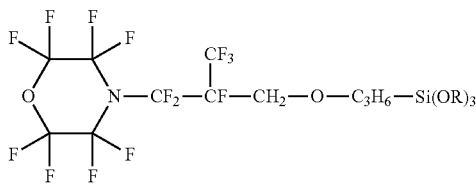 (A21)
[Chemical formula 93]
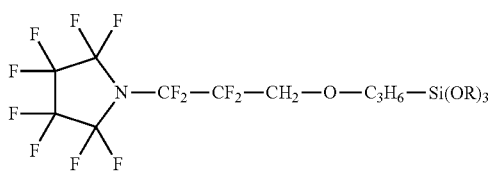 (A22)
[Chemical formula 94]
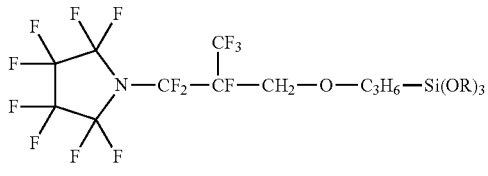 (A23)
[Chemical formula 95]
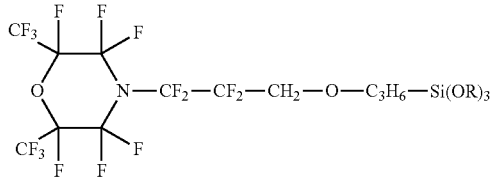 (A24)
[Chemical formula 96]
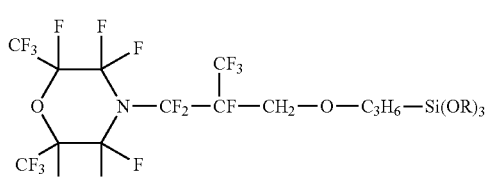 (A25)
[Chemical formula 97]
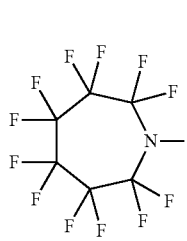 (A26)
[Chemical formula 98]
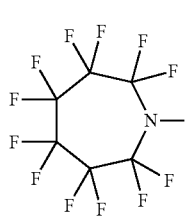 (A27)
[Chemical formula 99]
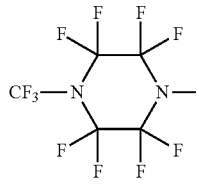 (A28)
[Chemical formula 100]
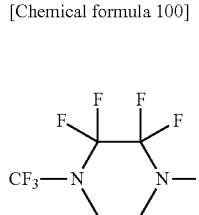 (A29)
[Chemical formula 101]
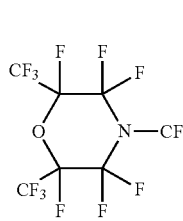 (A30)
[Chemical formula 102]
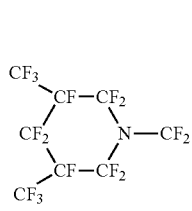 (A31)

[Chemical formula 103]
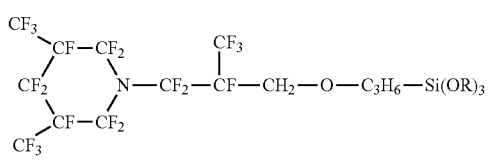
(A32)
[Chemical formula 104]
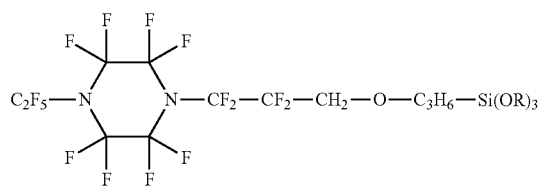
(A33)
[Chemical formula 105]
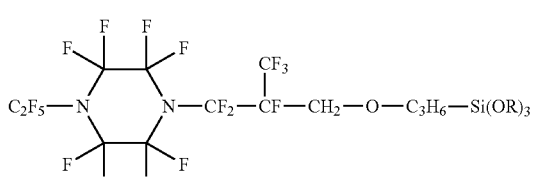
(A34)
[Chemical formula 106]
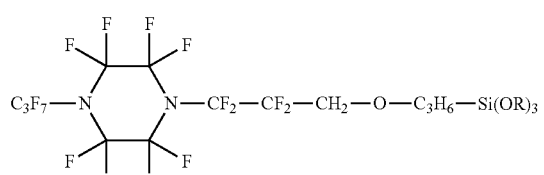
(A35)
[Chemical formula 107]
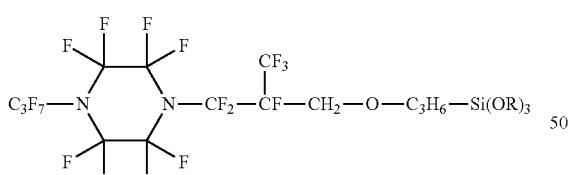
(A36)
[Chemical formula 108]
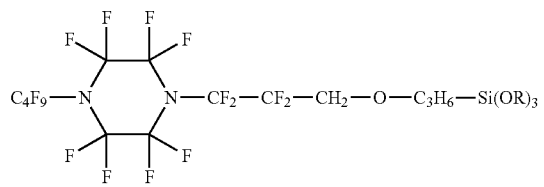
(A37)
[Chemical formula 109]
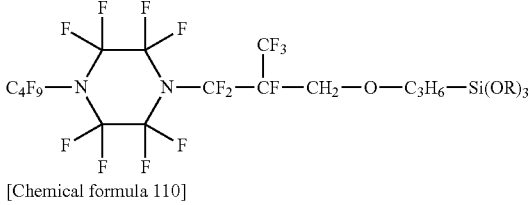
(A38)
[Chemical formula 110]
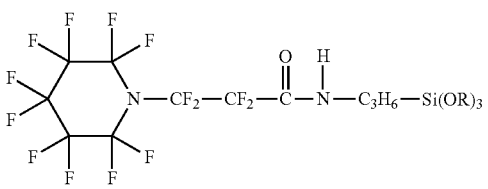
(A39)
[Chemical formula 111]
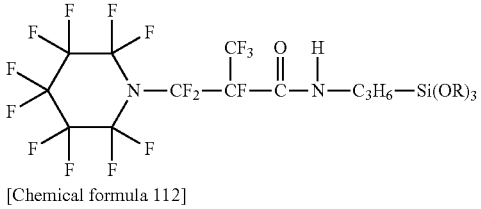
(A40)
[Chemical formula 112]
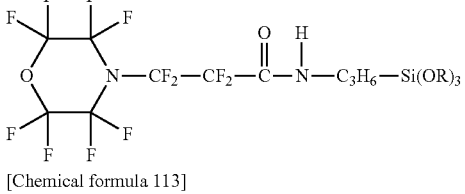
(A41)
[Chemical formula 113]
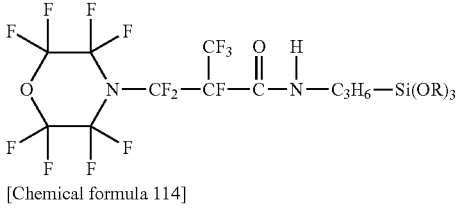
(A42)
[Chemical formula 114]
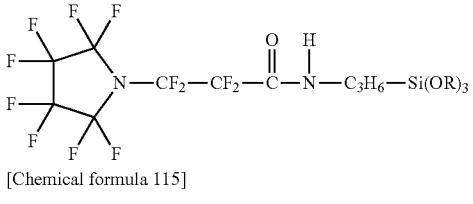
(A43)
[Chemical formula 115]
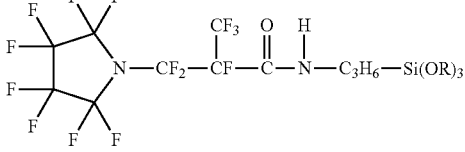
(A44)

-continued
[Chemical formula 116]
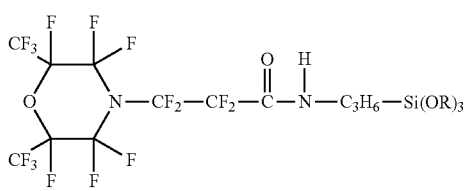
(A45)
[Chemical formula 117]
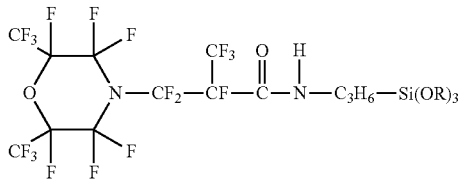
(A46)
[Chemical formula 118]
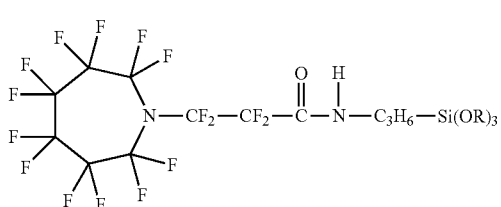
(A47)
[Chemical formula 119]
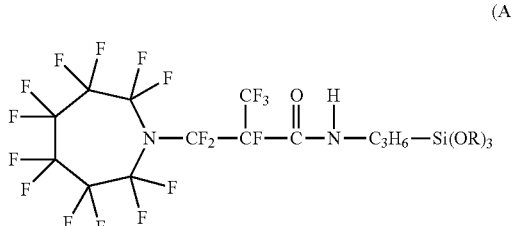
(A48)
[Chemical formula 120]
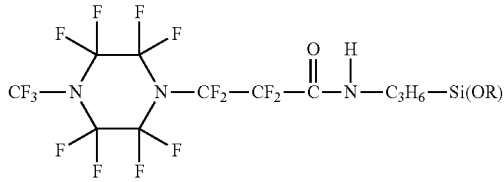
(A49)
[Chemical formula 121]
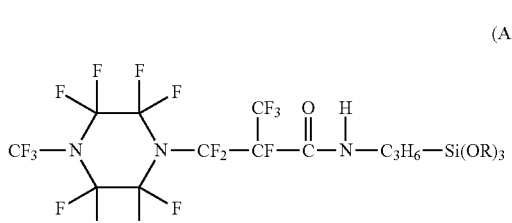
(A50)
-continued
[Chemical formula 122]
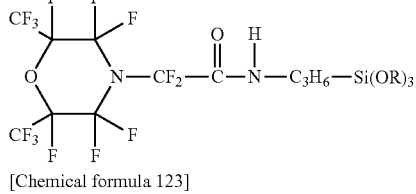
(A51)
[Chemical formula 123]
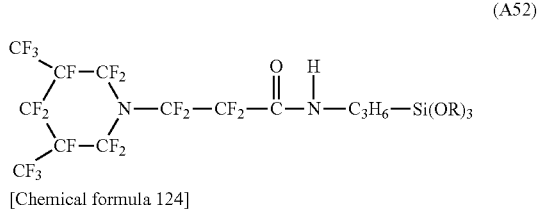
(A52)
[Chemical formula 124]
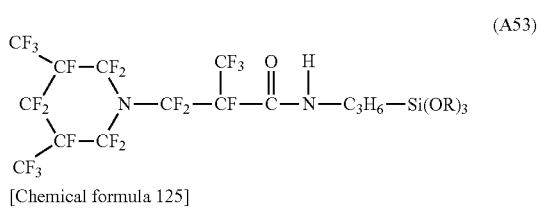
(A53)
[Chemical formula 125]
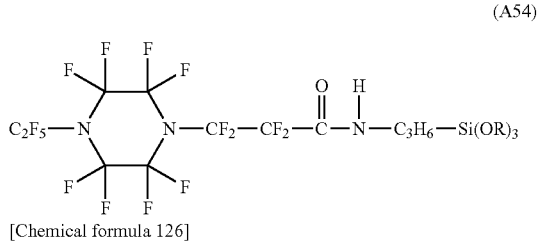
(A54)
[Chemical formula 126]
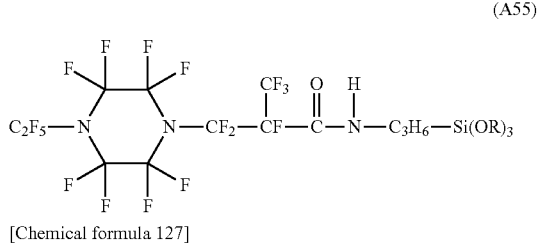
(A55)
[Chemical formula 127]
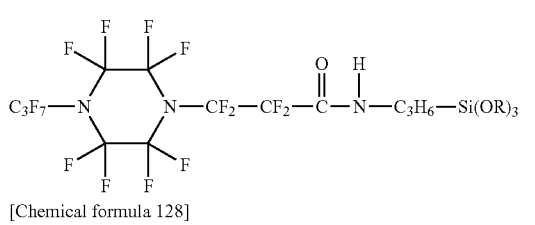
(A56)
[Chemical formula 128]
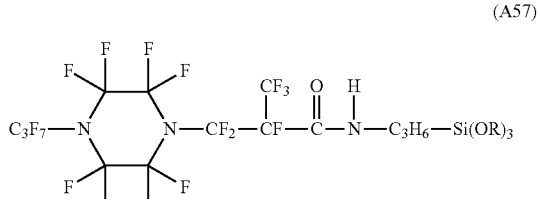
(A57)

[Chemical formula 129]
(A58)
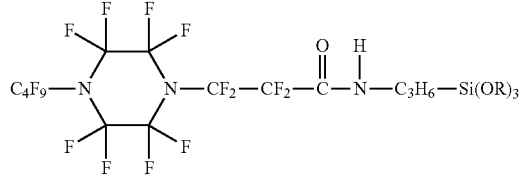
[Chemical formula 130]
(A59)
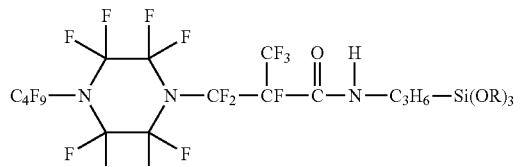
[Chemical formula 131]
(A60)
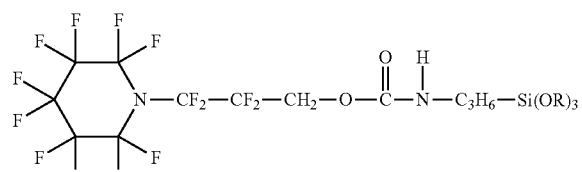
[Chemical formula 132]
(A61)
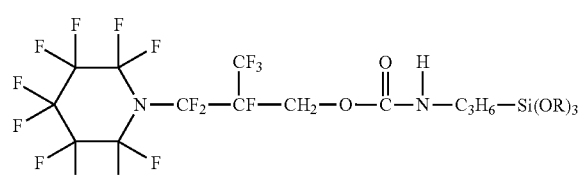
[Chemical formula 133]
(A62)
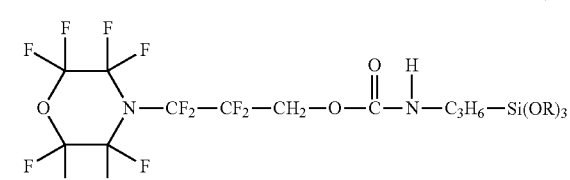
[Chemical formula 134]
(A63)
[Chemical formula 135]
(A64)
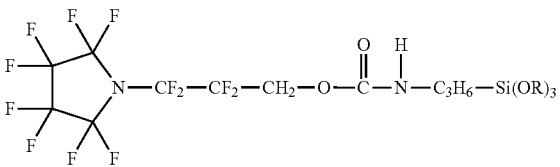
[Chemical formula 136]
(A65)
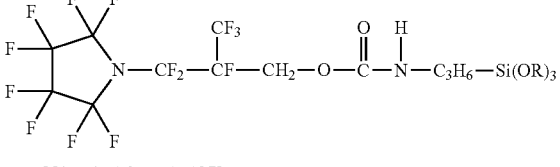
[Chemical formula 137]
(A66)
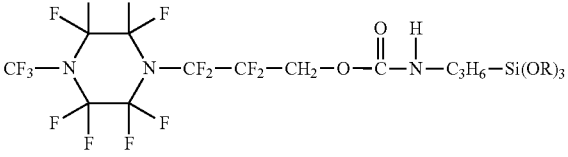
[Chemical formula 138]
(A67)
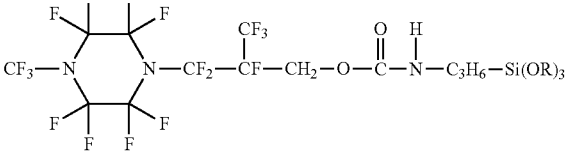
[Chemical formula 139]
(A68)
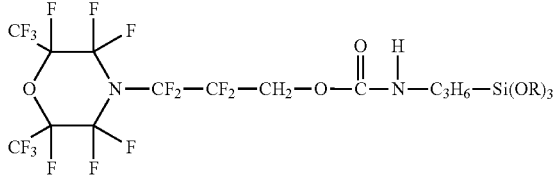
[Chemical formula 140]
(A69)
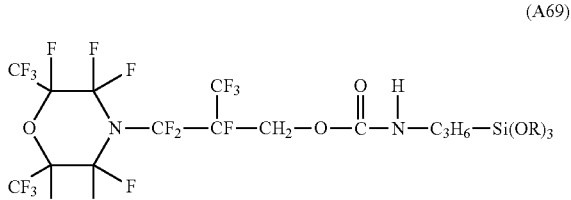

[Chemical formula 141]

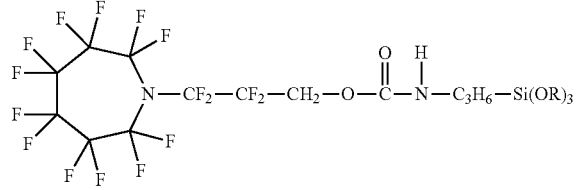
(A70)

[Chemical formula 142]

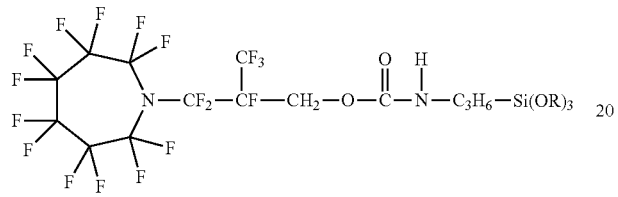
(A71)

[Chemical formula 143]

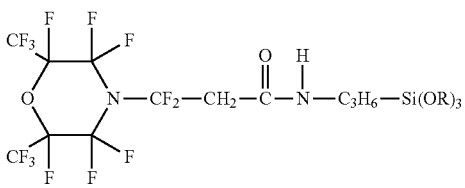
(A72)

[Chemical formula 144]

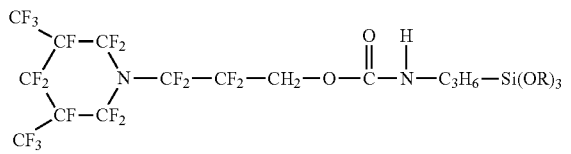
(A73)

[Chemical formula 145]

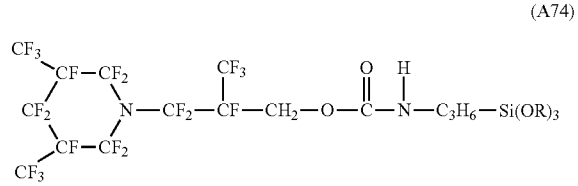
(A74)

[Chemical formula 146]

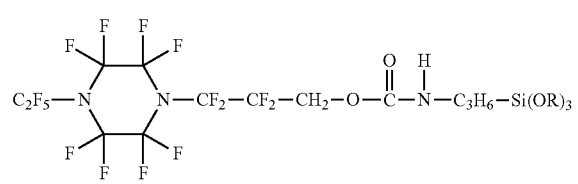
(A75)

[Chemical formula 147]

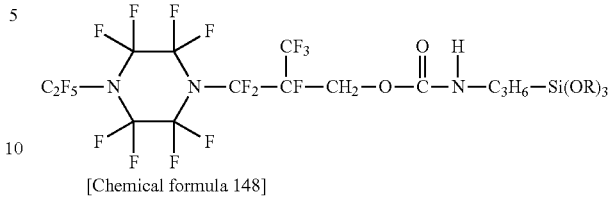
(A76)

[Chemical formula 148]

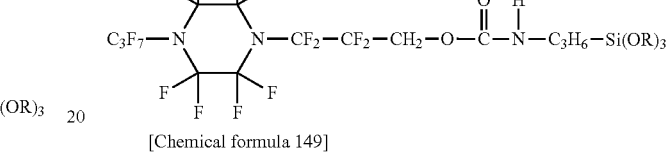
(A77)

[Chemical formula 149]

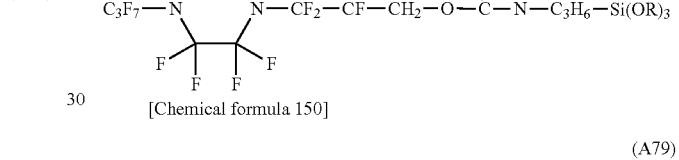
(A78)

[Chemical formula 150]

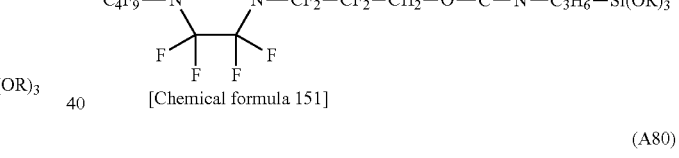
(A79)

[Chemical formula 151]

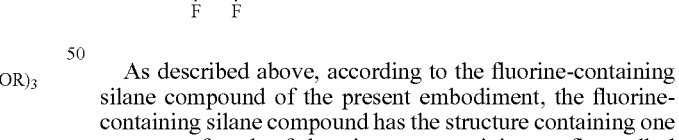
(A80)

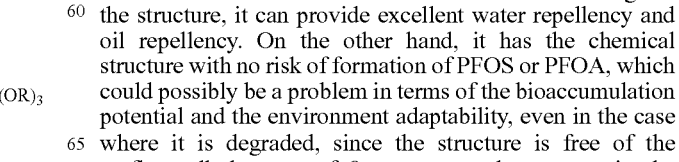

As described above, according to the fluorine-containing silane compound of the present embodiment, the fluorine-containing silane compound has the structure containing one or more of each of the nitrogen-containing perfluoroalkyl group and the alkoxysilyl group in the molecule. More specifically, the structure of the fluorine-containing silane compound contains the nitrogen-containing perfluoroalkyl group in which multiple short-chain length perfluoroalkyl groups of 6 or less carbon atoms are bonded to a nitrogen atom. Since the fluorine content in the molecule is high in the structure, it can provide excellent water repellency and oil repellency. On the other hand, it has the chemical structure with no risk of formation of PFOS or PFOA, which could possibly be a problem in terms of the bioaccumulation potential and the environment adaptability, even in the case where it is degraded, since the structure is free of the perfluoroalkyl group of 8 or more carbon atoms in the molecule.

As explained above, the fluorine-containing silane compound of the present embodiment is a novel compound having excellent properties, and useful as a fluorine-containing silane coupling agent. In other words, the fluorine-containing silane compound of the present embodiment is designed to satisfy both of the excellent water/oil repellency and the environment adaptability; and it cannot be conceived easily from the compound constituting the conventional fluorine-containing silane coupling agent.

In addition, the fluorine-containing silane compound of the present embodiment contains the perfluorinated heterocyclic ring. Since this perfluorinated heterocyclic ring has the ring structure and has packing effect between these ring structures, the fluorine-containing silane compound can provide the excellent properties such as: high water/oil repellency; high antifouling property; high fingerprint resistance; high releasing property; high moisture resistance; high water resistance; high heat resistance; and the like, due to the fluorine group, compared to the fluorine-containing silane compound having a straight-chain perfluoroalkyl structure of less carbon atoms, although it only contains the perfluoroalkyl group of the short-chain length structure.

[Method of Producing the Fluorine-Containing Silane Compound]

Next, an example of the method of producing the fluorine-containing silane compound of the present embodiment is explained.

In the method of producing the fluorine-containing silane compound of the present embodiment, the fluorine-containing silane compound is obtained: by reducing the carboxylic acid halide containing the nitrogen-containing perfluoroalkyl group represented by the formula (A81) shown below to alcohol; and by allowing the alcohol to react with isocyanate in the presence of a metallic catalyst after the reduction.

[Chemical formula 152]

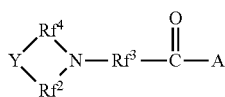

(A81)

In the formula (A81), $Rf^4$, $Rf^2$, and $Rf^3$ are identical or different perfluoroalkylene groups of 1 to 6 carbon atoms. Each of them may be a straight-chain or a branched-chain. In addition, Y is an oxygen atom, a nitrogen atom, or a $CF_2$ group. In addition, A is a halogen atom selected from the group consisting of fluorine, chlorine, bromine, and iodine.

The carboxylic acid halide containing the nitrogen-containing perfluoroalkyl group represented by the formula (A81) shown above can be obtained by electrolytically fluorinating corresponding carboxylic acid ester or halide in hydrogen fluoride, for example. In the case where a halogen atom other than fluorine atom is used as the Y, it can be obtained: by performing hydrolysis treatment on the carboxylic acid fluoride containing the perfluoroalkyl group obtained by the above-described electrolytic fluorination to form the corresponding carboxylic acid; and then by allowing the formed carboxylic acid to react with a suitable halogenating agent (for example, thionyl chloride, oxalyl chloride, phosphoryl chloride, sulfuryl chloride, phosphorus trichloride, phosphorus pentachloride, phosphorus tribromide, phosphorus pentabromide, hydrogen bromide, hydrogen iodide, and the like) to derive the corresponding carboxylic acid halide, for example.

Cases, in which Xs are compounds having the ether bond, the amide bond, and the urethane bond in the general formula (A1), are explained below.

[Case, in which X is a Compound Having the Urethane Bond]

In this case, X can be synthesized by the two-step reaction below, for example.

[Reduction Reaction of the Carboxylic Halide]

The carboxylic acid halide represented by the formula (A81) is subjected to a reduction reaction by dropping a reducing agent, which is typified by lithium aluminum hydride ($LiAlH_4$), sodium borohydride ($NaBH_4$), and the like, to a solvent or a dispersed organic solvent, for example. By this reduction reaction, the alcohol represented by the formula (A82) below is obtained.

[Chemical formula 153]

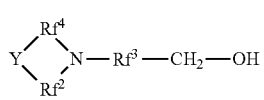

(A82)

In the formula (A82), $Rf^4$, $Rf^2$, and $Rf^3$ are identical or different perfluoroalkylene groups of 1 to 6 carbon atoms. Each of them may be a straight-chain or a branched-chain. In addition, Y is an oxygen atom, a nitrogen atom, or a $CF_2$ group.

[Reaction with Isocyanate]

The fluorine-containing silane compound represented by the general formula (A1) above is obtained by allowing the alcohol represented by the formula (A82) obtained by the above-described reduction reaction to react to trialkoxysilane, which is a silane coupling agent containing an isocyanate group in an organic solvent.

As examples of the silane coupling agent containing the isocyanate group, triethoxysilylpropyl isocyanate, trimethoxysilylpropyl isocyanate, and the like can be presented.

In the reaction, a catalyst may be added in order to accelerate the reaction. As specific examples, the metal catalyst such as dibutyltin dilaurate, dibutyltin diacetate, tin octylate, bismuth octylate, decanoic acid bismuth, lead naphthenate, potassium acetate, and the like; the amine-based catalyst such as triethylamine, tripropylamine, triethylenediamine, diazabicycloundecene, and the like; the trialkyl phosphine catalyst; and the like can be presented.

[Case, in which X is a Compound Having the Ether Bond]
[Formation of Allyl Ether Body]

In this case, first, the allyl ether body represented by the formula (A83) is obtained by allowing the alcohol represented by the formula (A82) obtained by reducing the carboxylic acid halide containing the fluoroalkyl group as in the case of the compound having the urethane bond, to react to allyl halide (for example, allyl bromide, allyl chloride, and the like).

[Chemical formula 154]

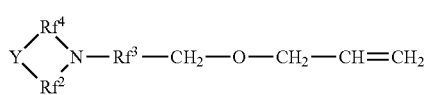

(A83)

[Hydrosilylation Reaction]

Next, the fluorine-containing silane compound represented by the general formula (A1) is obtained by allowing the obtained allyl ether body to react (hydrosilylation reaction using a platinum catalyst) to a silane compound (for example, trimethoxysilane, triethoxysilane, trichlorosilane, and the like).

[Case, in which X is a Compound Having the Amide Bond]
[Formation of Allyl Amide Body]

In this case, first, the allyl amide body represented by the formula (A84) below is obtained by allowing the carboxylic acid halide containing the nitrogen-containing perfluoroalkyl group represented by the formula (A81) above to react to allyl amine (for example, allyl amine, N-methyl allyl amine, and the like).

In the formula (A84) below, R is a hydrogen atom, a hydrocarbon group of 1 to 6 carbon atoms, or the like.

[Chemical formula 155]

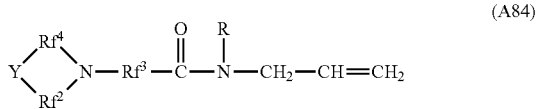

(A84)

[Hydrosilylation Reaction]

Next, the fluorine-containing silane compound represented by the general formula (A1) is obtained by allowing the obtained allyl amide body to react (hydrosilylation reaction using a platinum catalyst) to a silane compound (for example, trimethoxysilane, triethoxysilane, trichlorosilane, and the like).

[Utilization Method as a Fluorine-Containing Silane Coupling Agent]

Next, utilization method of the fluorine-containing silane compound as a fluorine-containing silane coupling agent is explained.

The fluorine-containing silane compound of the present embodiment can be used as a fluorine-containing silane coupling agent directly or after diluting by a medium as other component.

As the dilution medium used as the other component, liquid media such as organic solvents and water can be named. Specifically, as the concentration of the fluorine-containing silane compound in the dilution medium, it may be 0.01 to 100 mass %, for example. Preferably, the concentration is in the range of 0.01 to 50 mass %.

The organic solvent applicable to the fluorine-containing silane coupling agent of the present embodiment is not particularly limited. Specifically, the alcohol solvent such as methanol, ethanol, isopropyl alcohol, and the like; the ketone solvent such as acetone, methyl ethyl ketone; the ester solvent such as ethyl acetate, butyl acetate, and the like; the fluorine-based solvent such as α, α, α-trifluoro toluene, 1,3-bis trifluoromethyl benzene, 1,4-bis trifluoromethyl benzene, perfluorooctane, perfluorohexane, HCFC-225, HFC-365, methyl perfluoropropyl ether, methyl perfluoroalkyl ether, ethyl perfluorobutyl ether, hexafluoroisopropanol, and the like; and the like can used.

In addition, acid or alkaline (for example, hydrochloric acid, sulfuric acid, and nitric acid as the acid, and ammonia and the like as the alkaline) may be included in the fluorine-containing silane coupling agent other than the above-described fluorine-containing silane compound as the other component.

The fluorine-containing silane coupling agent of the present embodiment can be suitably used: as the coating agent providing properties such as effervescent, antifouling property, wiring resistance, water/oil repellency, releasing property, moisture resistance, water resistance, lubricity, heat resistance, and the like; as the surface preparation agent of the additives of the paint providing heat resistance; the migration inhibitor of the electronic components or circuits such as the silver paste, metal nano wiring, and the like; as the synthetic raw material of plastics; and the like.

Particularly, in the fluorine-containing silane coupling agent of the present embodiment, the fluorine-containing silane compound contains the perfluorinated heterocyclic ring structure as the nitrogen-containing perfluoroalkyl group. Since this perfluorinated heterocyclic ring has the ring structure and has packing effect between these ring structures, the fluorine-containing silane compound can provide the excellent properties such as: high water/oil repellency; high antifouling property; high fingerprint resistance; high releasing property; high moisture resistance; high water resistance; high heat resistance; and the like, due to the fluorine group, compared to the fluorine-containing silane coupling agent having a straight-chain perfluoroalkyl structure of less carbon atoms, although it only contains the perfluoroalkyl group of the short-chain length structure.

When it is used in applications, one kind of the fluorine-containing silane coupling agent of the present embodiment may be used. Alternatively, two different kinds of the fluorine-containing silane coupling agents may be used at the same time. Moreover, it may be used as a mixture with a component other than the fluorine-containing silane coupling agent.

As explained above, the fluorine-containing silane compound of the present embodiment is capable of providing excellent water repellency and oil repellency, and is useful as a fluorine-containing silane coupling agent with applicability to a wide variety of applications, even if it has a chemical structure, which is free of a perfluoroalkyl group of 8 or more of carbon atoms; and has no risk of formation of PFOS or PFOA causing bioaccumulation potential and environment adaptability problems.

The scope of the present invention is not limited by the descriptions of the first and second embodiments of the present invention, and can be modified in many ways as long as it is within the scope of the present invention.

EXAMPLES

The effect of the present invention is explained by Examples below in more detail. The present invention is not limited by the descriptions of Examples.

Example 1

Sodium borohydride (14.1 g) (manufactured by Tokyo Kasei Co., Ltd.) and tetrahydrofuran (310 ml) were fed to a three-necked flask with a dropping funnel. Then, $(CF_3CF_2CF_2CF_2)_2NCF_2CF_2COF$ (371.0 g, 70% purity), which was obtained by electrolytic fluorination of $(CH_3CH_2CH_2CH_2)_2NCH_2CH_2CO_2CH_3$, was fed in the dropping funnel and dropped slowly at room temperature.

After completion of the dropping, the content of the flask was stirred for an hour at room temperature. Then, the content of the flask was quenched by water and a hydrochloric acid aqueous solution, and separated by adding chloroform. Then, washing by a hydrochloric acid solution and water was performed on the obtained chloroform phase.

After drying the washed chloroform phase with magnesium sulfate, the obtained solution was concentrated by a rotary evaporator. Then, by distilling the obtained solution under reduced pressure, the alcohol body (171.0 g, yield: 68%) was obtained.

Next, the obtained alcohol body (200.0 g); and 3-isocyanate propyl triethoxy silane (70.7 g) (manufactured by Tokyo Kasei Co., Ltd.), acetonitrile (300 ml), and dibutyl tin dilaurate (3 drops) (manufactured by Wako Pure Chemical Industries, Ltd.), were mixed and the mixture was stirred for 4 hours at 70° C. Then, the obtained solution was concentrated by an evaporator. Finally, the fluorine-containing silane compound (233.5 g, yield: 98%) represented by the formula (70) was obtained by drying the concentrated solution under reduced pressure (2 Torr) at 140° C.

[Chemical formula 156]

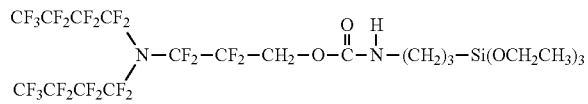

(70)

Example 2

The alcohol body (129.1 g), which was obtained as in Example 1; t-butanol (129.0 g) (Tokyo Kasei Co., Ltd.); and potassium t-butoxide (32.3 g) (manufactured by Wako Pure Chemical Industries, Ltd.) were fed to a three-necked flask with a dropping funnel. Then, allyl bromide (53.6 g) (manufactured by Wako Pure Chemical Industries, Ltd.) was fed in the dropping funnel and dropped slowly at 0° C.

After completion of the dropping, the content of the flask was stirred for an hour at room temperature. After filtering the reaction liquid, chloroform was added to the obtained filtrate. Then, washing by water was performed on the filtrate. After drying the washed filtrate with magnesium sulfate, the obtained solution was concentrated by a rotary evaporator. Then, by distilling the obtained solution under reduced pressure, the allyl ether (56.5 g, yield: 41%) was obtained.

Next, the obtained allyl ether (23.9 g); and toluene (50 ml), 1,3-divinyl-1,1,3,3-tetramethyldisiloxane platinum complex xylene solution (0.3 ml) (manufactured by Sigma-Aldrich), trimethoxysilane (5.6 g) (Tokyo Kasei Co., Ltd.), were mixed and the mixture was reacted for 4 hours at 60° C. Then, the obtained solution was concentrated by an evaporator. Finally, the fluorine-containing silane compound (15.0 g, yield: 53%) represented by the formula (71) was obtained by distilling under reduced pressure.

[Chemical formula 157]

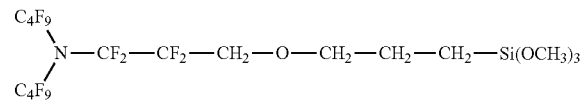

(71)

Example 3

Allyl amine (19.4 g) (manufactured by Wako Pure Chemical Industries, Ltd.) and diisopropyl ether (200 ml) were fed to a three-necked flask with a dropping funnel. Then, $(CF_3)_2NCF_2CF(CF_3)COF$ (63.3 g, 50% purity), which was obtained by electrolytic fluorination of $(CH_3)_2NCH_2CH(CH_3)CO_2CH_3$, was fed in the dropping funnel and dropped slowly at 0° C.

After completion of the dropping, the content of the flask was stirred for an hour at room temperature. Then, the reaction solution was washed by sodium hydroxide solution and water and dried with magnesium sulfate. After filtering off the magnesium sulfate, the obtained solution was concentrated by a rotary evaporator. Then, by distilling the obtained solution under reduced pressure, the allyl amide body (21.0 g, yield: 60%) was obtained.

Next, the obtained allyl amide body (14.7 g); and toluene (50 ml), 1,3-divinyl-1,1,3,3-tetramethyldisiloxane platinum complex xylene solution (0.3 ml) (manufactured by Sigma-Aldrich), and trimethoxysilane (5.6 g) (Tokyo Kasei Co., Ltd.), were mixed and the mixture was stirred for 4 hours at 60° C. Then, the obtained solution was concentrated by an evaporator. Finally, the fluorine-containing silane compound (15.1 g, yield: 78%) represented by the formula (72) was obtained by distilling under reduced pressure.

[Chemical formula 158]

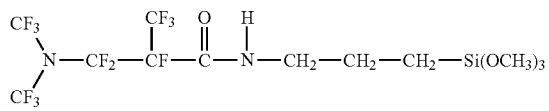

(72)

Comparative Example 1

The fluorine-containing silane compound ("trimethoxy (1H, 1H, 2H, 2H-heptadecafluorodecyl) silane" manufactured by Tokyo Kasei Kogyo Co., Ltd.) represented by the formula (73) was used as Comparative Example 1.

[Chemical formula 159]

$$C_8F_{17}-CH_2-CH_2-Si(OCH_3)_3 \quad (73)$$

Comparative Example 2

The fluorine-containing silane compound ("triethoxy (1H, 1H, 2H, 2H-nonafluorohexyl) silane" manufactured by Tokyo Kasei Kogyo Co., Ltd.) represented by the formula (74) was used as Comparative Example 2.

[Chemical formula 160]

$$C_4F_9-CH_2-CH_2-Si(OCH_2CH_3)_3 \quad (74)$$

[Verification Test]
[Water Repellency Evaluation as a Silane Coupling Agent]

In order to perform water repellency evaluation as a silane coupling agent on the fluorine-containing silane compounds synthesized in the above-described Examples 1 to 3, the contact angle measurement during contacting water was performed with Comparative Examples 1 to 2. The evaluation pieces were obtained by: using a slide glass for the object to be treated; dip-coating the slide glass with a solution in which the above-described fluorine-containing compound was dissolved in AK-225 (manufactured by Asahi Glass Co., Ltd.) at 2 mass %; and drying for one hour at 80° C. In the contact angle measurement: the contact angle meter, model CA-A manufactured by Kyowa Interface Chemical Co., Ltd. was used; the volume of the water droplet was 20 μl; the contact angle measurement was conducted at arbitrary 5 points on the surface-treated piece; and the average value of the 5 points was calculated. The evaluation result is shown in Table 1 below.
[Oil Repellency Evaluation of Oil-Based Pen]

In order to perform the oil repellency evaluation of the oil-based pen ("Magic Ink" manufactured by Uchida Yoko co., Ltd.) as a silane coupling agent on the fluorine-containing silane compounds synthesized in the above-described Examples 1 to 3, the oil repellency was evaluated when the oil-based pen was applied on with the above-described Comparative Examples 1 to 2. The evaluation pieces were prepared as in the above-described in the water repellency evaluation. A straight line of 1 cm long was drawn on the surface of the evaluation piece with the oil-based pen; and the repellency was evaluated visually based on the following criteria. The evaluation results were shown in Table 1 below.
 ○: repellency is observed fully
 Δ: repellency is observed partially
 x: no repellency is observed

TABLE 1

|  | Water contact angle | Repellency of oil-based pen |
| --- | --- | --- |
| Example 1 | 111° | ○ |
| Example 2 | 106° | ○ |
| Example 3 | 114° | Δ |
| Comparative Example 1 | 110° | Δ |
| Comparative Example 2 | 95° | x |

As shown in Table 1, it was demonstrated that the fluorine-containing silane compounds of the present invention (Examples 1 to 3) had excellent properties (water/oil repellency), since even though they did not contain the perfluoroalkyl group of 8 or more carbon atoms, they showed equivalent or even better water contact angles and oil repellency of the oil-based pen. In addition, it was demonstrated that the properties of the fluorine-containing silane compounds of the present invention (Examples 1 to 3) were superior to Comparative Example 2 with less carbon atoms.

Example 4

Sodium borohydride (18.6 g) (manufactured by Tokyo Kasei Co., Ltd.) and tetrahydrofuran (400 ml) were fed to a three-necked flask with a dropping funnel. Then, O(CF(CF$_3$)CF$_2$)$_2$NCF$_2$COF (350.0 g, 60% purity), which was obtained by electrolytic fluorination of O(CH(CH$_3$)CH$_2$)$_2$NCH$_2$CO$_2$CH$_3$, was fed in the dropping funnel and dropped slowly at room temperature.

After completion of the dropping, the content of the flask was stirred for an hour at room temperature. Then, the content of the flask was quenched by water and a hydrochloric acid aqueous solution, and separated by adding chloroform. Then, washing by a hydrochloric acid solution and water was performed on the obtained chloroform phase. After drying the washed chloroform phase with magnesium sulfate, the obtained solution was concentrated by a rotary evaporator. Then, by distilling the obtained solution under reduced pressure, the alcohol body (131.4 g, yield: 65%) was obtained.

Next, the obtained alcohol body (100.0 g); and 3-isocyanate propyl triethoxy silane (50.2 g) (manufactured by Tokyo Kasei Co., Ltd.), acetonitrile (230 ml), and dibutyl tin dilaurate (3 drops) (manufactured by Wako Pure Chemical Industries, Ltd.), were mixed and the mixture was stirred for 4 hours at 70° C. Then, the obtained solution was concentrated by an evaporator. Finally, the fluorine-containing silane compound (130.7 g, yield: 98%) represented by the formula (A85) was obtained by drying the concentrated solution under reduced pressure (2 Torr) at 140° C.

[Chemical formula 161]

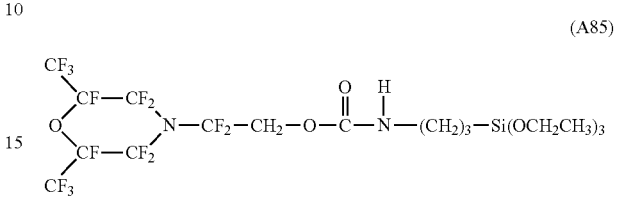

(A85)

Example 5

The alcohol body (150.0 g), which was obtained as in Example 4; t-butanol (150.0 g) (Tokyo Kasei Co., Ltd.); and potassium t-butoxide (53.2 g) (manufactured by Wako Pure Chemical Industries, Ltd.) were fed to a three-necked flask with a dropping funnel. Then, allyl bromide (88.3 g) (manufactured by Wako Pure Chemical Industries, Ltd.) was fed in the dropping funnel and dropped slowly at 0° C.

After completion of the dropping, the content of the flask was stirred for an hour at room temperature. After filtering the reaction liquid, chloroform was added to the obtained filtrate. Then, washing by water was performed on the filtrate. After drying the washed filtrate with magnesium sulfate, the obtained solution was concentrated by a rotary evaporator. Then, by distilling the obtained solution under reduced pressure, the allyl ether (84.0 g, yield: 51%) was obtained.

Next, the obtained allyl ether (20.0 g); and toluene (50 ml), 1,3-divinyl-1,1,3,3-tetramethyldisiloxane platinum complex xylene solution (0.3 ml) (manufactured by Sigma-Aldrich), trimethoxysilane (6.5 g) (Tokyo Kasei Co., Ltd.), were mixed and the mixture was reacted for 4 hours at 60° C. Then, the obtained solution was concentrated by an evaporator. Finally, the fluorine-containing silane compound (15.2 g, yield: 60%) represented by the formula (A86) was obtained by distilling under reduced pressure.

[Chemical formula 162]

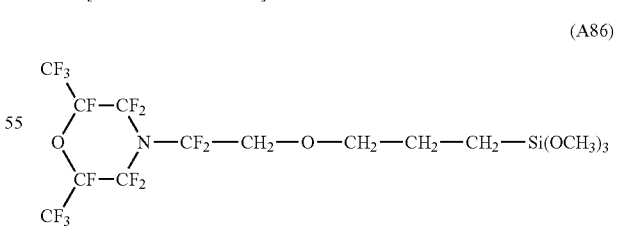

(A86)

Comparative Example 3

The fluorine-containing silane compound ("trimethoxy (1H, 1H, 2H, 2H-heptadecafluorodecyl) silane" manufactured by Tokyo Kasei Kogyo Co., Ltd.) represented by the formula (A87) was used as Comparative Example 3.

[Chemical formula 163]

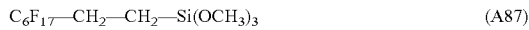

Comparative Example 4

The fluorine-containing silane compound ("triethoxy (1H, 1H, 2H, 2H-nonafluorohexyl) silane" manufactured by Tokyo Kasei Kogyo Co., Ltd.) represented by the formula (A88) was used as Comparative Example 4.

[Chemical formula 164]

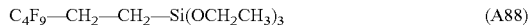

[Verification Test]
[Water Repellency Evaluation as a Silane Coupling Agent]

In order to perform water repellency evaluation as a silane coupling agent on the fluorine-containing silane compounds synthesized in the above-described Examples 4 and 5, the contact angle measurement during contacting water was performed with Comparative Examples 3 to 4. The evaluation pieces were obtained by: using a slide glass for the object to be treated; dip-coating the slide glass with a solution in which the above-described fluorine-containing compound was dissolved in AK-225 (manufactured by Asahi Glass Co., Ltd.) at 2 mass %; and drying for one hour at 80° C. In the contact angle measurement: the contact angle meter, model CA-A manufactured by Kyowa Interface Chemical Co., Ltd. was used; the volume of the water droplet was 20 µl; the contact angle measurement was conducted at arbitrary 5 points on the surface-treated piece; and the average value of the 5 points was calculated. The evaluation result is shown in Table 2 below.

[Oil Repellency Evaluation of Oil-Based Pen]

In order to perform the oil repellency evaluation of the oil-based pen ("Magic Ink" manufactured by Uchida Yoko co., Ltd.) as a silane coupling agent on the fluorine-containing silane compounds synthesized in the above-described Examples 4 and 5, the oil repellency was evaluated when the oil-based pen was applied on with the above-described Comparative Examples 3 to 4. The evaluation pieces were prepared as in the above-described in the water repellency evaluation. A straight line of 1 cm long was drawn on the surface of the evaluation piece with the oil-based pen; and the repellency was evaluated visually based on the following criteria. The evaluation results were shown in Table 2 below.
○: repellency is observed fully
Δ: repellency is observed partially
x: no repellency is observed

TABLE 2

|   | Water contact angle | Repellency of oil-based pen |
|---|---|---|
| Example 4 | 111° | ○ |
| Example 5 | 106° | ○ |
| Comparative Example 3 | 110° | Δ |
| Comparative Example 4 | 95° | x |

As shown in Table 2, it was demonstrated that the fluorine-containing silane compounds of the present invention (Examples 4 and 5) had excellent properties (water/oil repellency), since even though they did not contain the perfluoroalkyl group of 8 or more carbon atoms, they showed equivalent or even better water contact angles and oil repellency of the oil-based pen. In addition, it was demonstrated that the properties of the fluorine-containing silane compounds of the present invention (Examples 4 and 5) were superior to Comparative Example 3 with less carbon atoms.

INDUSTRIAL APPLICABILITY

The fluorine-containing silane compound of the present invention has: excellent water/oil repellency; low bioaccumulation potential; and excellent environment adaptability. Thus, the fluorine-containing silane compound of the present invention is useful as a fluorine-containing silane coupling agent with applicability to a wide variety of applications such as the surface preparation agent, the coating agent, the coating material, and the like.

The invention claimed is:
1. A fluorine-containing silane compound comprising a perfluoroamine structure represented by a general formula (1) or a general formula (A1) below,

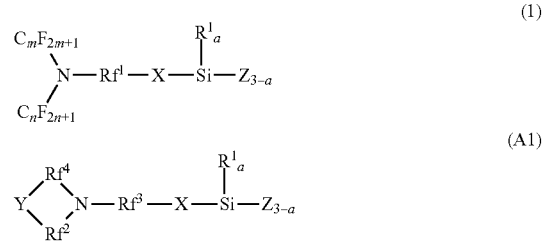

wherein, in the general formula (1), m and n are integers from 1 to 6, which are identical or different; $Rf^1$ is a straight-chain or a branched-chain perfluoroalkylene group of 1 to 6 carbon atoms,
in the general formula (A 1), $Rf^2$, $Rf^3$, and $Rf^4$ are straight-chain or branched-chain perfluoroalkylene groups of 1 to 6 carbon atoms,
in the general formula (1) and the general formula (A1), X is a hydrocarbon group of 2 to 10 carbon atoms and includes one or more selected from an ether bond, a CO—NH bond, and an O—CO—NH bond,
in the general formula (1) and the general formula (A1), $R^1$ and Z are an alkoxy group or a halogen group, a being an integer from 0 to 3, and
in the general formula (A1), Y is an oxygen atom, a nitrogen atom, or a $CF_2$ group.
2. The fluorine-containing silane compound according to claim 1, wherein Z is an alkoxy group.

* * * * *